United States Patent
Brannan et al.

(10) Patent No.: US 10,111,718 B2
(45) Date of Patent: *Oct. 30, 2018

(54) MICROWAVE ABLATION SYSTEM WITH USER-CONTROLLED ABLATION SIZE AND METHOD OF USE

(71) Applicant: COVIDIEN LP, Mansfield, MA (US)

(72) Inventors: Joseph D. Brannan, Lyons, CO (US); Kyle R. Rick, Boulder, CO (US)

(73) Assignee: Covidien LP, Mansfield, MA (US)

( * ) Notice: Subject to any disclaimer, the term of this patent is extended or adjusted under 35 U.S.C. 154(b) by 157 days.

This patent is subject to a terminal disclaimer.

(21) Appl. No.: 15/055,009

(22) Filed: Feb. 26, 2016

(65) Prior Publication Data

US 2016/0175046 A1   Jun. 23, 2016

Related U.S. Application Data

(63) Continuation of application No. 14/036,006, filed on Sep. 25, 2013, now Pat. No. 9,867,670, which is a (Continued)

(51) Int. Cl.
*A61B 18/18* (2006.01)
*A61B 34/00* (2016.01)
(Continued)

(52) U.S. Cl.
CPC .............. *A61B 34/25* (2016.02); *A61B 18/18* (2013.01); *A61B 18/1815* (2013.01); (Continued)

(58) Field of Classification Search
USPC .................................................. 606/33, 41
See application file for complete search history.

(56) References Cited

U.S. PATENT DOCUMENTS 3,631,363 A   12/1971   Miller
4,397,313 A    8/1983   Vaguine
(Continued)

FOREIGN PATENT DOCUMENTS

DE         390937 C   3/1924
DE        1099658 B   2/1961
(Continued)

OTHER PUBLICATIONS

Australian Examination Report issued in Appl. No. AU 2016202454 dated May 22, 2017.
(Continued)

*Primary Examiner* — Nicole F Johnson

(57) ABSTRACT

Disclosed is a system and method for enabling user preview and control of the size and shape of an electromagnetic energy field used in a surgical procedure. The disclosed system includes a selectively activatable source of microwave surgical energy in the range of about 900 mHz to about 5 gHz in operable communication with a graphical user interface and a database. The database is populated with data corresponding to the various surgical probes, such as microwave ablation antenna probes, that may include a probe identifier, the probe diameter, operational frequency of the probe, ablation length of the probe, ablation diameter of the probe, a temporal coefficient, a shape metric, and the like. The probe data is graphically presented on the graphical user interface where the surgeon may interactively view and select an appropriate surgical probe. Three-dimensional views of the probe(s) may be presented allowing the surgeon to interactively rotate the displayed image.

16 Claims, 9 Drawing Sheets

Related U.S. Application Data continuation of application No. 12/416,583, filed on Apr. 1, 2009, now Pat. No. 9,277,969.

(51) Int. Cl.

| | | |
|---|---|---|
| *A61B 34/10* | (2016.01) | |
| *G06F 3/0481* | (2013.01) | |
| *G06F 3/0484* | (2013.01) | |
| *G06F 17/30* | (2006.01) | |
| *G06T 13/20* | (2011.01) | |
| *G06T 15/00* | (2011.01) | |
| *G06T 19/00* | (2011.01) | |
| *A61B 90/90* | (2016.01) | |

(52) U.S. Cl.
CPC .......... *A61B 34/10* (2016.02); *G06F 3/04815* (2013.01); *G06F 3/04842* (2013.01); *G06F 3/04845* (2013.01); *G06F 17/3028* (2013.01); *G06T 13/20* (2013.01); *G06T 15/00* (2013.01); *G06T 19/003* (2013.01); *A61B 90/90* (2016.02); *A61B 2034/101* (2016.02); *A61B 2034/104* (2016.02); *A61B 2034/105* (2016.02); *A61B 2034/107* (2016.02)

(56) References Cited

U.S. PATENT DOCUMENTS

| | | | |
|---|---|---|---|
| 4,462,412 A | 7/1984 | Turner | |
| 4,572,190 A | 2/1986 | Azam et al. | |
| 4,798,215 A | 1/1989 | Turner | |
| 5,097,844 A | 3/1992 | Turner | |
| 5,417,210 A | 5/1995 | Funda et al. | |
| 5,472,441 A | 12/1995 | Edwards et al. | |
| 5,800,484 A | 9/1998 | Gough et al. | |
| 5,863,290 A | 1/1999 | Gough et al. | |
| 5,904,709 A | 5/1999 | Arndt et al. | |
| 5,951,547 A | 9/1999 | Gough et al. | |
| 6,031,375 A | 2/2000 | Atalar et al. | |
| 6,073,051 A | 6/2000 | Sharkey et al. | |
| 6,241,725 B1* | 6/2001 | Cosman ............. A61B 18/1477 600/41 | |
| 6,245,065 B1 | 6/2001 | Panescu et al. | |
| 6,246,898 B1 | 6/2001 | Vesely et al. | |
| 6,273,886 B1 | 8/2001 | Edwards et al. | |
| 6,350,276 B1 | 2/2002 | Knowlton | |
| 6,358,245 B1 | 3/2002 | Edwards et al. | |
| 6,375,606 B1 | 4/2002 | Garibaldi et al. | |
| 6,451,015 B1 | 9/2002 | Rittman, III et al. | |
| 6,464,689 B1 | 10/2002 | Qin et al. | |
| 6,506,189 B1 | 1/2003 | Rittman, III et al. | |
| 6,551,311 B2 | 4/2003 | Lee et al. | |
| 6,575,969 B1 | 6/2003 | Rittman, III et al. | |
| 6,603,994 B2 | 8/2003 | Wallace et al. | |
| 6,622,731 B2 | 9/2003 | Daniel et al. | |
| 6,725,080 B2 | 4/2004 | Melkent et al. | |
| 6,783,523 B2 | 8/2004 | Qin et al. | |
| 6,994,704 B2 | 2/2006 | Qin et al. | |
| 7,025,765 B2 | 4/2006 | Balbierz et al. | |
| 7,108,696 B2 | 9/2006 | Daniel et al. | |
| 7,122,031 B2 | 10/2006 | Edwards et al. | |
| 7,160,296 B2 | 1/2007 | Pearson et al. | |
| 7,282,050 B2 | 10/2007 | Starkebaum et al. | |
| 7,344,533 B2 | 3/2008 | Pearson et al. | |
| 7,400,930 B2 | 7/2008 | Sharkey et al. | |
| 7,419,487 B2 | 9/2008 | Johnson et al. | |
| 7,439,736 B2 | 10/2008 | Meaney et al. | |
| 7,467,015 B2 | 12/2008 | van der Weide | |
| 7,565,207 B2 | 7/2009 | Turner et al. | |
| 9,277,969 B2 | 3/2016 | Brannan et al. | |
| 2002/0022836 A1 | 2/2002 | Goble et al. | |
| 2003/0097130 A1 | 5/2003 | Muller et al. | |
| 2003/0199755 A1 | 10/2003 | Halperin et al. | |
| 2003/0199863 A1 | 10/2003 | Swanson et al. | |
| 2004/0097805 A1 | 5/2004 | Verard et al. | |
| 2004/0147920 A1 | 7/2004 | Keidar | |
| 2004/0167392 A1 | 8/2004 | Halperin et al. | |
| 2004/0242992 A1 | 12/2004 | Hareyama | |
| 2005/0205566 A1 | 9/2005 | Kassayan | |
| 2005/0228251 A1 | 10/2005 | Grabb et al. | |
| 2006/0106375 A1 | 5/2006 | Werneth et al. | |
| 2006/0289528 A1 | 12/2006 | Chiu et al. | |
| 2007/0066971 A1 | 3/2007 | Podhajsky | |
| 2007/0100405 A1 | 5/2007 | Thompson et al. | |
| 2007/0118101 A1 | 5/2007 | Mahesh et al. | |
| 2007/0124128 A1 | 5/2007 | Connacher et al. | |
| 2007/0191825 A1 | 8/2007 | Cronin et al. | |
| 2008/0015664 A1 | 1/2008 | Podhajsky | |
| 2008/0183165 A1 | 7/2008 | Buysse et al. | |
| 2008/0319434 A1 | 12/2008 | Rick et al. | |
| 2009/0221999 A1* | 9/2009 | Shahidi .................. A61B 18/18 606/33 |
| 2010/0157018 A1* | 6/2010 | Lampotang ............ G06F 3/011 348/36 |

FOREIGN PATENT DOCUMENTS

| | | |
|---|---|---|
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 481 685 A1 | 4/1992 |
| EP | 0 521 264 A2 | 1/1993 |
| EP | 0541930 A1 | 5/1993 |
| EP | 0 556 705 A1 | 8/1993 |
| EP | 0 558 429 A1 | 9/1993 |
| EP | 0572131 A1 | 12/1993 |
| EP | 0 836 868 A2 | 4/1998 |
| EP | 1278007 A1 | 1/2003 |
| EP | 1159926 A3 | 3/2003 |
| EP | 1 810 627 A1 | 7/2007 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |

(56) References Cited

FOREIGN PATENT DOCUMENTS

| | | |
|---|---|---|
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 7-47079 | 2/1995 |
| JP | 07265328 A | 10/1995 |
| JP | 08056955 | 3/1996 |
| JP | 08252263 A | 10/1996 |
| JP | 09010223 | 1/1997 |
| JP | 11244298 A | 9/1999 |
| JP | 2000-210300 A | 8/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| JP | 2007-135894 A | 6/2007 |
| JP | 2007-144180 A | 6/2007 |
| JP | 2007-155348 A | 6/2007 |
| JP | 2009-018169 A | 1/2009 |
| JP | 05-123327 B2 | 1/2013 |
| SU | 166452 | 1/1965 |
| SU | 401367 A1 | 10/1973 |
| SU | 727201 A2 | 4/1980 |
| WO | 96/34571 A1 | 11/1996 |
| WO | 97/41924 A1 | 11/1997 |
| WO | 97/43971 A2 | 11/1997 |
| WO | 00/48672 A1 | 8/2000 |
| WO | 00/51513 A1 | 9/2000 |
| WO | 00/53113 A1 | 9/2000 |
| WO | 01/01847 A1 | 1/2001 |
| WO | 01/74252 A2 | 10/2001 |
| WO | 02/45790 A2 | 6/2002 |
| WO | 02/061880 A2 | 8/2002 |
| WO | 2004/112628 A1 | 12/2004 |
| WO | 2005/016119 A2 | 2/2005 |
| WO | 2007/059172 A2 | 5/2007 |
| WO | 2007/129308 A2 | 11/2007 |
| WO | 2008/090484 A2 | 7/2008 |
| WO | 2010/064154 A1 | 6/2010 |

OTHER PUBLICATIONS

Japanese Office Action from Appl. No. JP 2014-122359 dated Feb. 20, 2017.
Japanese Office Action for Japanese Appln. No. JP 2016-038576 dated Nov. 25, 2016.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/ Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Cosman et al., "Methods of Making Nervous System Lesions" in William RH, Rengachary SS (eds): Neurosurgery, New York: McGraw. cndot.Hill, vol. 111, (1984), pp. 2490-2499.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Venous Complex" Sales/Product Literature 2000.

(56) References Cited

OTHER PUBLICATIONS

Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure. TM. Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
Esterline Product Literature, "Light Key: Visualize a Virtual Keyboard. One With No Moving Parts", Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report EP 10158944 dated Jun. 21, 2010.
U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
Japanese Office Action and English language translation issued in Appl. No. JP 2016-038576 dated Apr. 6, 2017.
Extended European Search Report for EP 16 19 7971 dated Feb. 22, 2017.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.

(56) References Cited

OTHER PUBLICATIONS

International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
European Search Report for EP10158944 dated Jun. 10, 2010.
Japanese Office Action, and English translation, dated Jul. 10, 2015 from Application No. JP 2014-122359.
Japanese Office Action dated Apr. 7, 2015 from Application No. JP 2014-122359.
Extended European Search Report dated Apr. 14, 2015 from Application No. EP 14196930.3.
Australian Patent Examination Report No. 1 from Appl. No. AU 2014202855 dated Jul. 21, 2015.
Notice of Final Rejection from Japanese Appl. No. 2014-122359 dated Nov. 2, 2015.
Japanese Pre-Appeal Examination Report for JP 2014-122359 dated Mar. 28, 2016.
Jarrett et al., "Use of the LigaSure.TM. Vessel Sealing System for Peri-Hilar Vessels in Laparoscopic Nephrectomy" Sales/Product Literature 2000.
Johnson, "Evaluation of the LigaSure.TM. Vessel Sealing System in Hemorrhoidectormy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
Mdtech product literature (Mar. 2000) I'D Wire: product description, 1 page.
Mdtech product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, OApr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
S. Humphries Jr. et al., "Finite.cndot.Element Codes to Model Electrical Heating and Non.cndot.Llnear Thermal Transport in Biological Media", Proc. ASME HTD-355, 131 (1997).

(56) References Cited

OTHER PUBLICATIONS

Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
Notice of Final Rejection, with English language translation, issued in Japanese Appl. No. 2016-038576 dated Jul. 21, 2017.
Japanese Notice of Allowance dated Dec. 18, 2017 issued in corresponding JP Appln. No. 2016-038576. (Summary only).
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.

\* cited by examiner

MICROWAVE ABLATION SYSTEM WITH USER-CONTROLLED ABLATION SIZE AND METHOD OF USE

The present application is a continuation of U.S. patent application Ser. No. 14/036,006, filed Sep. 25, 2103 which is a continuation of U.S. patent application Ser. No. 12/416,583, filed Apr. 1, 2009, the entire contents of which are incorporated by reference herein.

BACKGROUND

1. Technical Field

The present disclosure relates to systems and methods for providing energy to biological tissue and, more particularly, to systems and methods for enabling user selection of the size and shape of a microwave energy field used in a surgical procedure.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator. In tissue ablation electrosurgery, the radio frequency energy may be delivered to targeted tissue by an antenna or probe.

In the case of tissue ablation, a high radio frequency energy in the range of about 300 mHz to about 300 gHz is applied to a targeted tissue site to create an ablation volume, which may have a particular size and shape. The particular type of tissue ablation procedure may dictate a particular ablation volume in order to achieve the desired surgical outcome. By way of example, and without limitation, a spinal ablation procedure may call for a longer, more narrow ablation volume, whereas in a prostate ablation procedure, a more spherical ablation volume may be required.

The ablation volume may be affected by various factors, including without limitation, probe construction, antenna size and shape, frequency, energy level, energy delivery method, and duration of energy delivery. Conventionally, a surgeon must rely upon professional experience and published specifications to select an ablation probe and related electrosurgical parameters with which to achieve a desired ablation volume for a particular patient.

SUMMARY

The present disclosure provides an electromagnetic surgical ablation system having a generator assembly that includes generator module that is configured to provide radiofrequency surgical energy, such as electrosurgical or microwave energy. A processor is included in the generator assembly that is operably coupled to the generator module and a user interface. The user interface may include a graphic touchscreen display, as well as switches and illuminated indicators. The user interface displays a graphical representation of a surgical instrument, such as without limitation a microwave antenna probe. The graphical representation includes an image corresponding to the instrument's radiating field, such as without limitation an antenna probe ablation pattern. The disclosed system includes a database in operable communication with the processor that is adapted to store probe parameters corresponding to at least one antenna probe. A user, typically a surgeon, may then use the user interface to graphically view various probe parameters stored within the database, and thereby choose an appropriate instrument (e.g., ablation probe) with which to perform a surgical procedure. In an embodiment, a shape selection user interface element is provided to receive a shape selection input, which may reflect the surgeon's choice of instrument. In an embodiment, an identifier within the selected probe is recognized by the generator assembly to confirm the actual probe used by the surgeon corresponds to the selected probe.

In some embodiments, a three-dimensional view of a probe and an ablation pattern corresponding thereto is displayed on the user interface. A rotation user interface element may be provided by the user interface, wherein rotation the user interface element is configured to accept an input which causes the user interface to rotate the displayed three dimensional view. In some embodiments, a temporal user interface element is provided by the user interface that is configured to accept a temporal user input which, in response thereto, causes the graphical display to present an animation representative of a change in a probe parameter with respect to time.

Also provided is a method for computer-assisted surgical instrument selection, comprised of providing a selectively-activatable source of electromagnetic surgical energy that includes a user interface, and providing a database in operable communication with the source of electromagnetic energy. The database is populated with at least one surgical instrument parameter and at least one identification parameter associated with a surgical instrument. A visual representation is generated of at least one instrument parameter and displayed on the user interface. At least one associated identification parameter associated with a surgical instrument (e.g., a model number or a clinical designation) may also be displayed. A surgeon responds to the visual display by selecting, with the user interface, a desired surgical instrument. The surgeon activates the source of electromagnetic surgical energy to supply electromagnetic surgical energy to the selected surgical instrument. A surgeon may view a plurality of probe images prior to making a selection.

Also disclosed is a computer-readable medium storing a set of programmable instructions configured for being executed by at least one processor for performing a method for computer-assisted surgical instrument selection as described herein.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
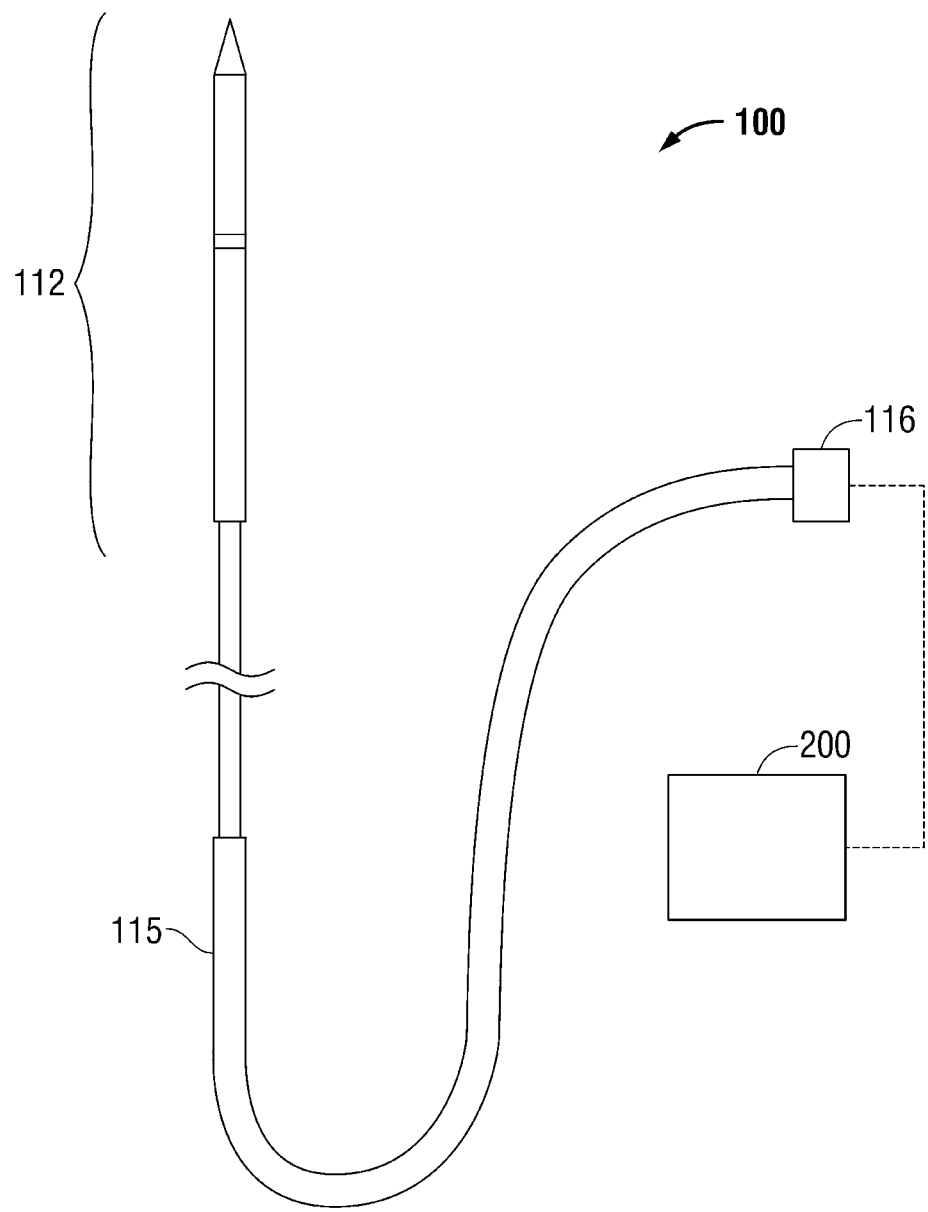
FIG. 1 shows a diagram of a microwave ablation system having a microwave antenna assembly in accordance with the present disclosure.

Particular embodiments of the present disclosure will be described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user.

FIG. 1 shows an embodiment of a microwave ablation system 100 in accordance with the present disclosure. The microwave ablation system 100 includes a microwave antenna probe 112 connected by a cable 115 to connector 116, which may further operably connect the antenna probe 112 to a generator assembly 200 configured to provide, e.g., microwave or RF energy in a range of about 915 mHz to about 2450 mHz. Antenna probe 112, as shown, is a dipole microwave antenna assembly, but other antenna assemblies, e.g., choked, wet-tip, monopole or leaky wave antenna assemblies, may also utilize the principles set forth herein.

Figure 2:
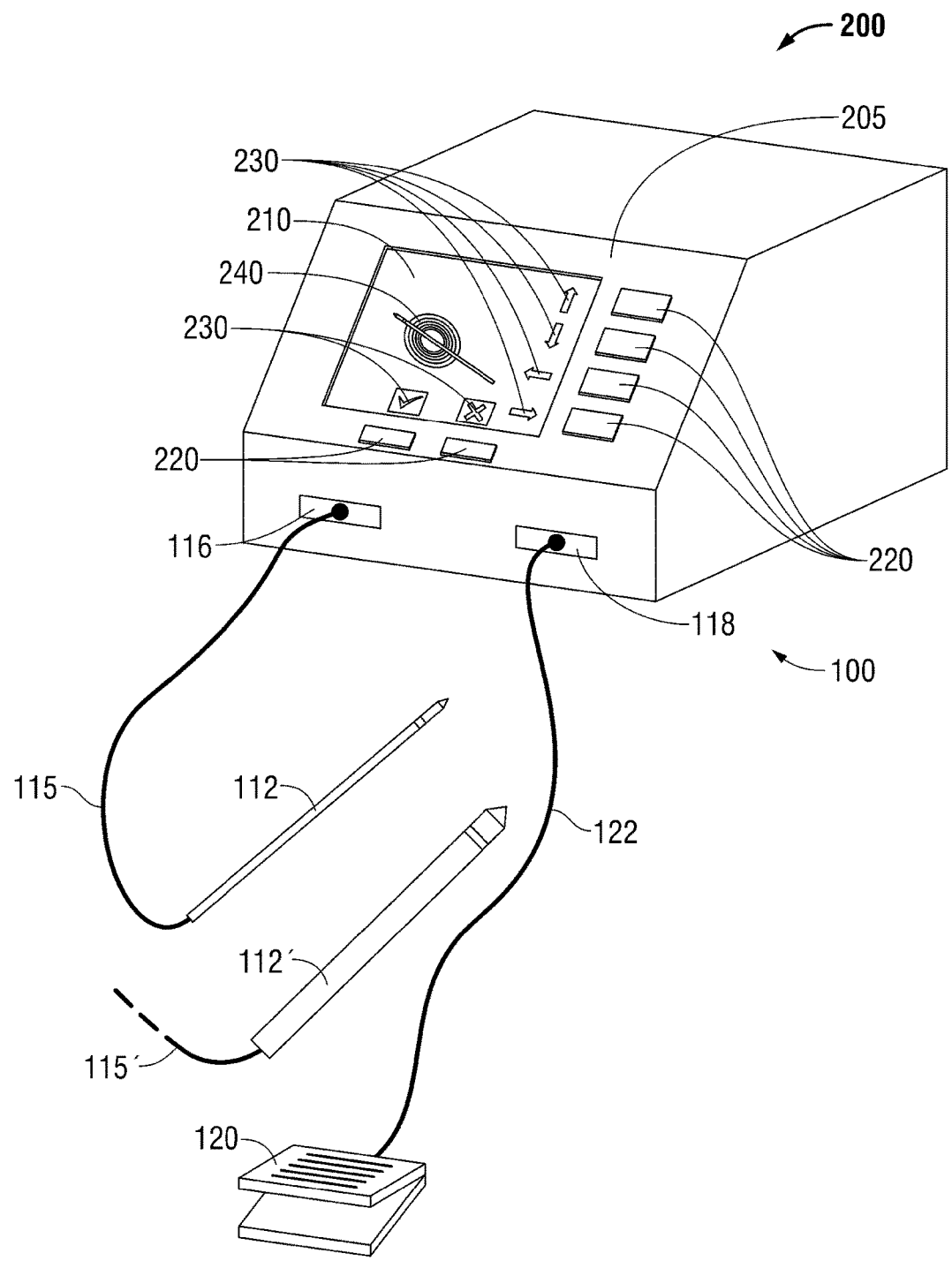
FIG. 2 shows a diagram of a microwave ablation system that includes a user interface for displaying and controlling ablation patterns in accordance with the present disclosure.

In greater detail, FIG. 2 illustrates a microwave ablation system 100 in accordance with the present disclosure. The disclosed system includes an actuator 120, which may be a footswitch, a handswitch, a bite-activated switch, or any other suitable actuator. Actuator 120 is operably coupled by a cable 122 via connector 118 to generator assembly 200. Cable 122 may include one or more electrical conductors for conveying an actuation signal from actuator 120 to generator assembly 200. In an embodiment, actuator 120 is operably coupled to generator assembly 200 by a wireless link, such as without limitation, a radiofrequency or infrared link. At least one additional or alternative microwave antenna probe 112' may be included with microwave ablation system 100 that may have characteristics distinct from that of microwave antenna probe 112. For example without limitation, microwave antenna probe 112 may be a 12 gauge probe suitable for use with energy of about 915 mHz, while microwave antenna probe 112' may be a 14 gauge probe suitable for use with energy of about 915 mHz. Other probe variations are contemplated within the scope of the present disclosure, for example without limitation, a 12 gauge operable at 2450 mHz, and a 14 gauge operable at 2450 mHz. In use, the user, typically a surgeon, may interact with user interface 205 to preview operational characteristics of available probes 112, 112' et seq., and to choose a probe for use in accordance with surgical requirements.

Generator assembly 200 includes a generator module 286 in operable communication with processor 282 that is configured as a source of RF and/or microwave energy. In an embodiment, generator module 286 is configured to provide energy of about 915 mHz. Generator module 286 may also be configured to provide energy of about 2450 mHz (2.45 gHz.) The present disclosure contemplates embodiments wherein generator module 286 is configure to generate a frequency other than about 915 mHz or about 2450 mHz, and embodiments wherein generator module is configured to generate variable frequency energy. Probe 112 is operably coupled to an energy output of generator module 286.

Actuator 120 is operably coupled to processor 282 via user interface 210. In embodiments, actuator 120 may be operably coupled to processor, and/or to generator 286 by a cable connection, or a wireless connection.

Generator assembly 200 also includes user interface 205, that may include a display 210 such as, without limitation, a flat panel graphic LCD display, adapted to visually display at least one user interface element 230, 240. In an embodiment, display 210 includes touchscreen capability (not explicitly shown), e.g., the ability to receive input from an object in physical contact with the display, such as without limitation a stylus or a user's fingertip, as will be familiar to the skilled practitioner. A user interface element 230, 240 may have a corresponding active region, such that, by touching the screen within the active region associated with the user interface element, an input associated with the user interface element is received by the user interface 205.

User interface 205 may additionally or alternatively include one or more controls 220, that may include without limitation a switch (e.g., pushbutton switch, toggle switch, slide switch) and/or a continuous actuator (e.g., rotary or linear potentiometer, rotary or linear encoder.) In an embodiment, a control 220 has a dedicated function, e.g., display contrast, power on/off, and the like. Control 220 may also have a function which may vary in accordance with an operational mode of the ablation system 100. A user interface element 230 may be positioned substantially adjacently to control 220 to indicate the function thereof. Control 220 may also include an indicator, such as an illuminated indicator (e.g., a single- or variably-colored LED indicator.)

Figure 3:
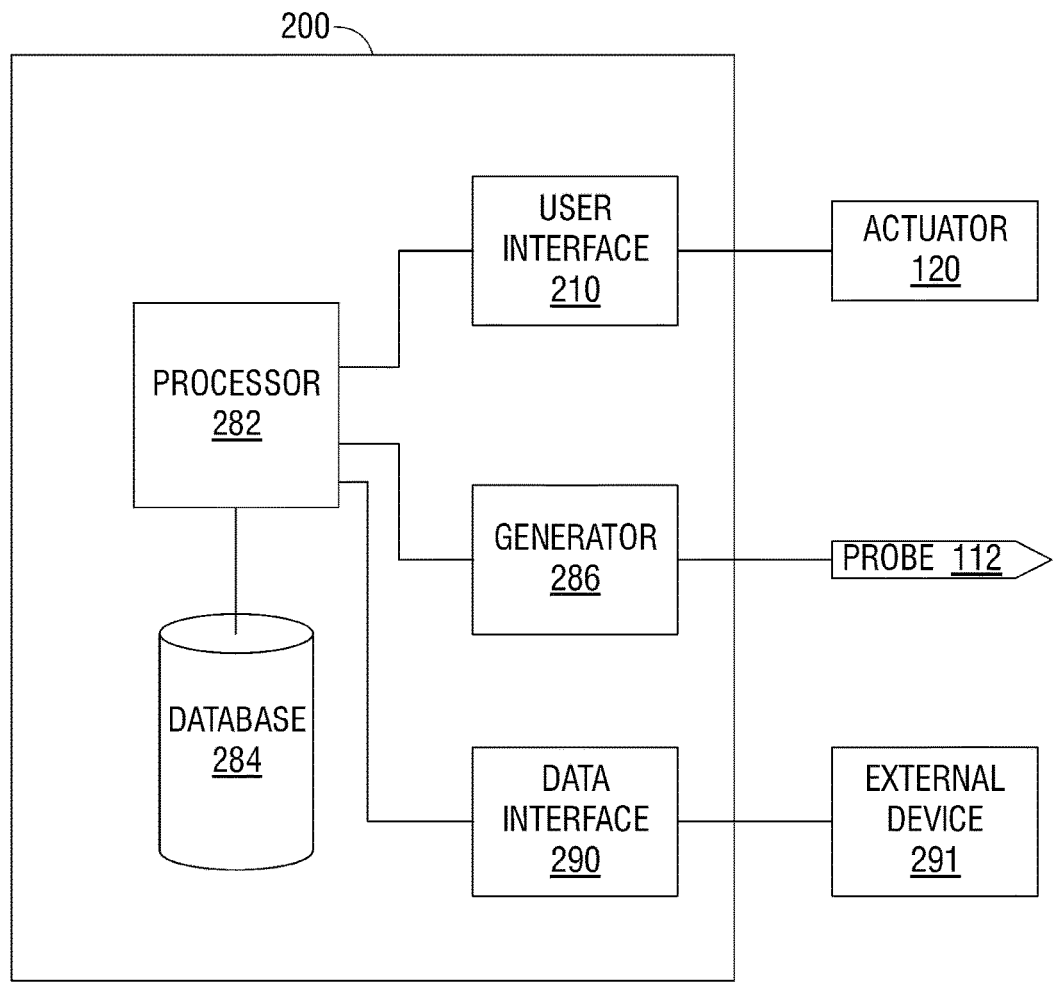
FIG. 3 is a block diagram of a microwave ablation system in accordance with the present disclosure.

Turning now to FIG. 3, generator assembly 200 includes a processor 282 that is operably coupled to user interface 210. A storage device 288 is operably coupled to processor 282, and may include random-access memory (RAM), read-only memory (ROM), and/or non-volatile memory (NV-RAM, Flash, and disc-based storage.) Storage device 288 may include a set of program instructions executable on processor 282 for executing a method for displaying and controlling ablation patterns in accordance with the present disclosure. Generator assembly 200 may include a data interface 290 that is configure to provide a communications link to an external device 291. In an embodiment, data interface 290 may be any of a USB interface, a memory card slot (e.g., SD slot), and/or a network interface (e.g., 100BaseT Ethernet interface or an 802.11 "WiFi" interface.) External device 291 may be any of a USB device (e.g., a memory stick), a memory card (e.g., an SD card), and/or a network-connected device (e.g., computer or server.) Generator assembly 200 may also include a database 284 that is configured to store and retrieve probe data, e.g., parameters associated with one or more probes 112. Parameters stored in database 284 in connection with a probe may include, but are not limited to, probe identifier, a probe diameter, a frequency, an ablation length, an ablation diameter, a temporal coefficient, a shape metric, and/or a frequency metric. In an embodiment, ablation pattern topology may be included in database 284, e.g., a wireframe model of a probe 112 and/or an ablation pattern associated therewith.

Database 284 may also be maintained at least in part by data provided by external device 291 via data interface 290. For example without limitation, probe data may be uploaded from an external device 291 to database 284 via data interface 290. Additionally or alternatively, probe data may be manipulated, e.g., added, modified, or deleted, in accordance with data and/or instructions stored on external device 291. In an embodiment, the set of probe data represented in database 284 is automatically synchronized with corresponding data contained in external device 291 in response to external device 291 being coupled (e.g., physical coupling and/or logical coupling) to data interface 290.

Processor 282 is programmed to enable a user, via user interface 205 and/or display 210, to view at least one ablation pattern and/or other probe data corresponding to a probe 112 et seq. For example, a surgeon may determine that a substantially spherical ablation pattern is necessary. The surgeon may activate a "select ablation shape" mode of operation for generator assembly 200, preview a number of probes by reviewing graphically and textually presented data on display 210, optionally or alternatively manipulate a graphic image by, for example, rotating the image, and to select an appropriate probe 112 et seq. based upon displayed parameters. The selected probe may then be coupled to generator assembly 200 for use therewith. In an embodiment, probe 112 may include an identifier (not explicitly shown) that provides an identification signal to generator assembly 200 to facilitate confirmation that a particular probe 112 of the selected type is coupled to generator assembly 200.

In an embodiment, a surgeon may input via user interface 205 a probe parameter to cause generator assembly 200 to present at least one probe corresponding thereto. For example, a surgeon may require a 3.0 cm diameter ablation pattern, and provide an input corresponding thereto. In response, the generator assembly 200 may preview a corresponding subset of available probes that match or correlate to the inputted parameter.

Figure 4A:
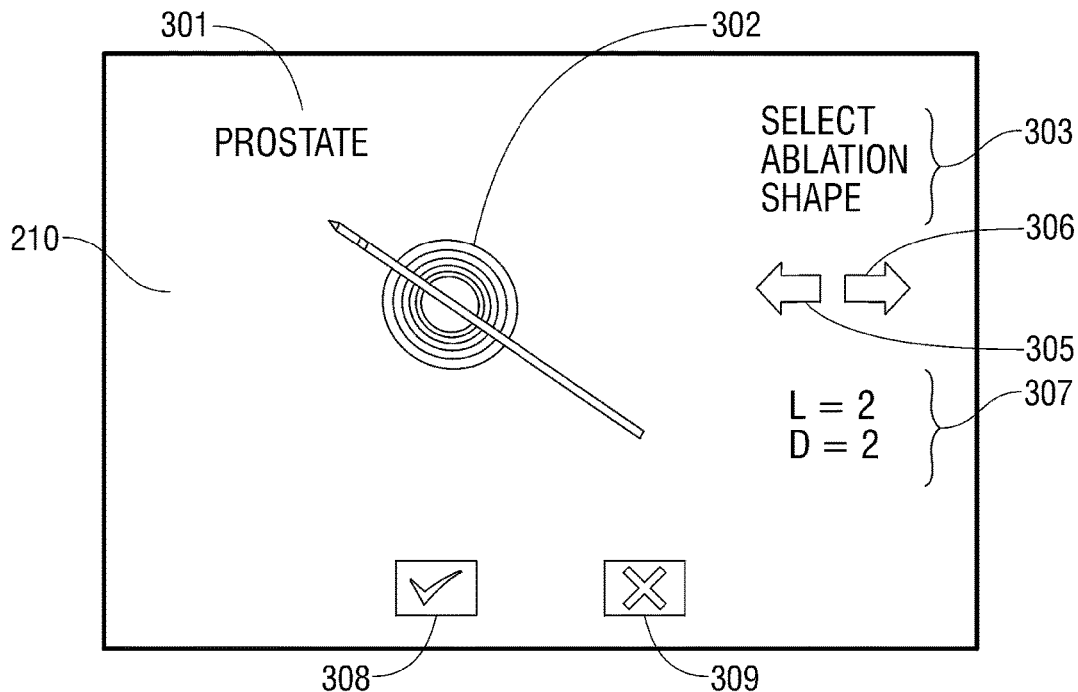
FIG. 4A shows a user interface in accordance with the present disclosure wherein a side view of a first ablation pattern is displayed.

Turning now to FIGS. 4A-4D, generator assembly 200 provides a user interface 210 which may present a probe image 302. Probe image 302 may be a three dimensional (e.g., 3D) graphic rendering of the characteristics of probe 112 that are stored in database 284. Probe image 302 may be rendered using any suitable rendering technique, such as wire-frame projections and/or ray-tracing. User interface 210 provides a select ablation shape indicator 303, which may be a graphic icon or a textual command, that informs the user that generator assembly 200 is in a probe selection mode (e.g., probe select and/or ablation shape selection mode). A shape selection user interface element 305, 306 may be provided for receiving a shape selection user input thereby enabling a user to choose an ablation shape from among one of a set of ablation shapes and/or probes stored in database 282. A probe designation 301 (e.g., probe name) may be displayed. As seen in FIG. 4A, a shape selection user interface element 305, 306 may include a graphic icon, such as without limitation, an arrowhead, and/or may include textual commands, such as "previous" or "next."

Additional parameters 307 of one or more displayed probes 112 may be presented on display 210, which may include probe diameter, frequency, ablation length, ablation diameter, and/or shape metric. A shape metric is defined as a minimum ablation diameter expressed as a percentage of a maximum ablation diameter, e.g., $100(d_{min}/d_{max})$, where $d_{min}$ is a minimum ablation diameter and $d_{max}$ is a maximum ablation diameter.

Figure 4B:
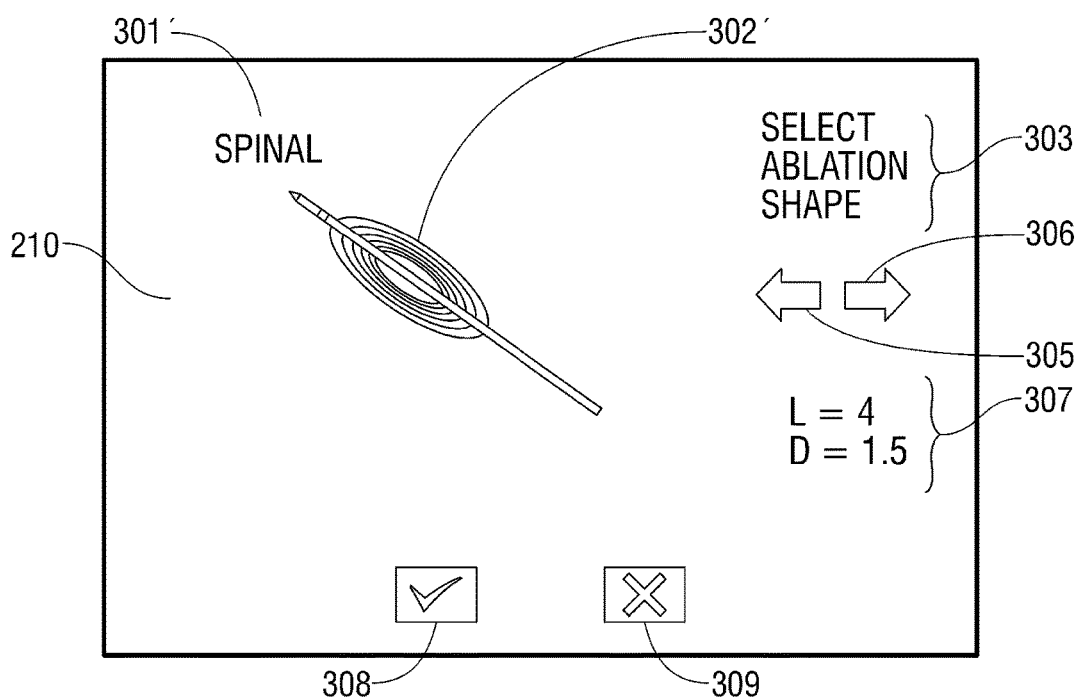
FIG. 4B shows a user interface in accordance with the present disclosure wherein a side view of a second ablation pattern is displayed.

By actuating a shape selection icon, a user may cause display 210 to depict characteristics of a different probe 112 as stored in database 282. For example, as shown in FIG. 4B, a user has made a shape selection by activating a shape selection user interface element 305, 306, causing an characteristics of an alternative probe 302' to be displayed. The corresponding user interface elements are updated accordingly, such that, as seen in FIG. 4B, the corresponding probe designation 301', probe image 302'; and additional parameters 307' correctly reflect characteristics of the currently-displayed probe.

Figure 4C:
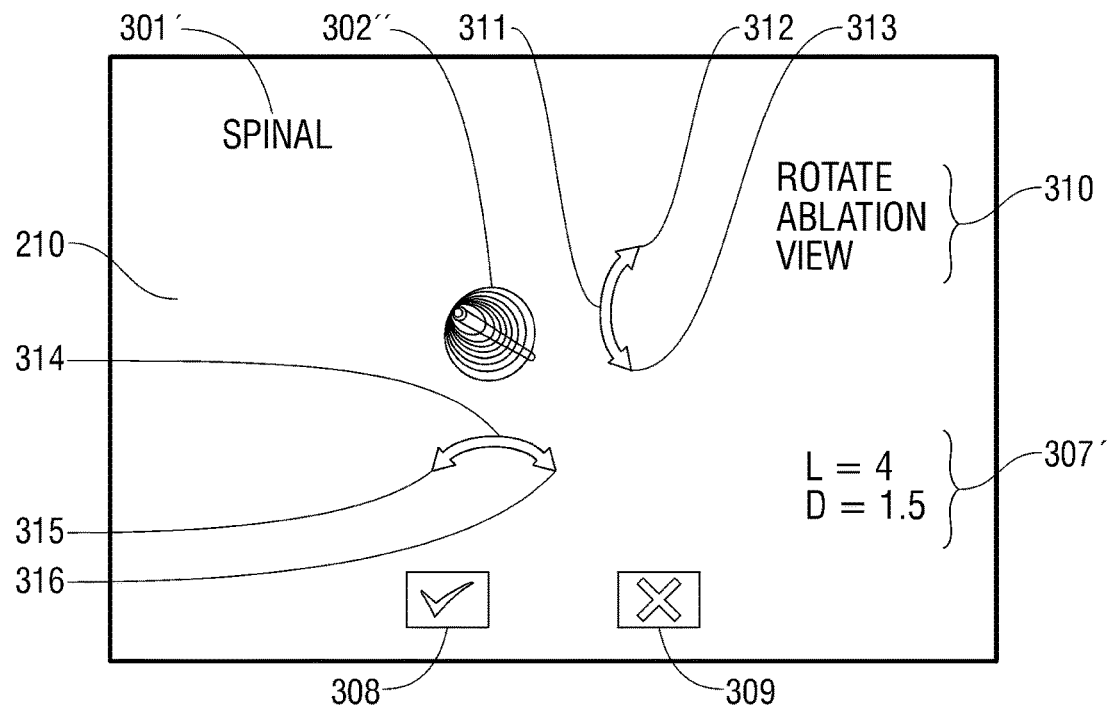
FIG. 4C shows a user interface in accordance with the present disclosure wherein an oblique view of a second ablation pattern is displayed.
Figure 4D:
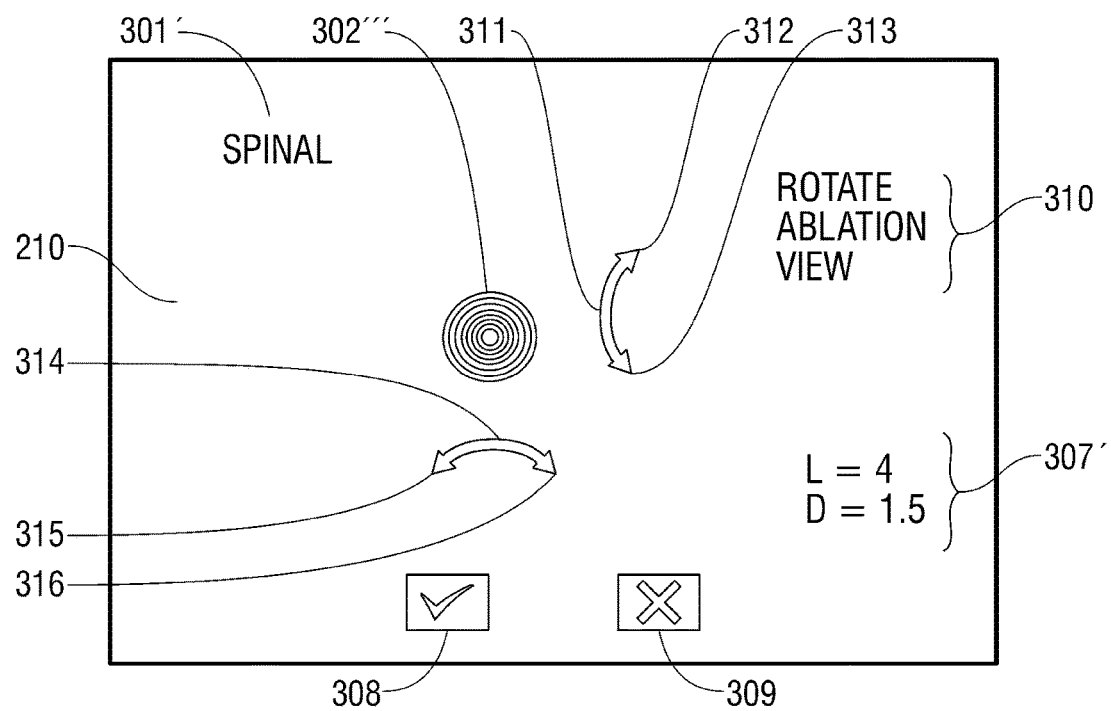
FIG. 4D shows a user interface in accordance with the present disclosure wherein an axial view of a second ablation pattern is displayed.

As shown in FIGS. 4C and 4D, the user may activate a rotate ablation image mode of display for generator assembly 200 wherein a rotation user interface element 312, 314 may be used to display alternate probe image views 302", 302''' in response to receiving a rotation user input. In an embodiment, rotation user interface element 312, 314 may be a hidden and/or invisible region of display 210, permitting the user to cause the probe image 302' to be rotated by, for example, wiping a fingertip on the display 210 (e.g., gesturing) to indicate the direction and axis of rotation. Rotation user interface element 312, 314 may be visible and include arrowheads 311, 313, 315, 316 to denote upward rotation, downward rotation, left rotation, and right rotation, respectively, of probe image 302'.

In an embodiment, at least one patient image, e.g., ultrasound, CT scan, MRI, and the like, (not explicitly shown) may be presented on display 210 over which a displayed probe 302 is superimposed thereupon to enable the user to visualize an ablation pattern of a probe 302 in situ with surrounding tissue. The patient image may be a 3D image and responsive to an input received by rotation user interface element 312, 314, such that the patient image and displayed probe 302 rotate together in a substantially synchronized manner to enable a user to visualize the relationship of the probe 302, ablation pattern thereof and surrounding tissue from a plurality of viewing angles.

A temporal user interface element (not explicitly shown) may be provided to enable a user to view changes in an ablation pattern over time. Temporal user interface element may include, for example, a slider, which may be positioned at a desired point along a time scale to view an ablation pattern corresponding thereto. In an embodiment, actuation of a temporal user interface element may cause an animated depiction of an ablation pattern to be displayed. Such animation may be displayed in real-time, slower than real-time, or faster than real-time.

A user may confirm a probe choice by activating an accept selection user interface element 308, or exit a probe selection mode without making a selection by activating a cancel selection user interface element 309.

Figure 5A:
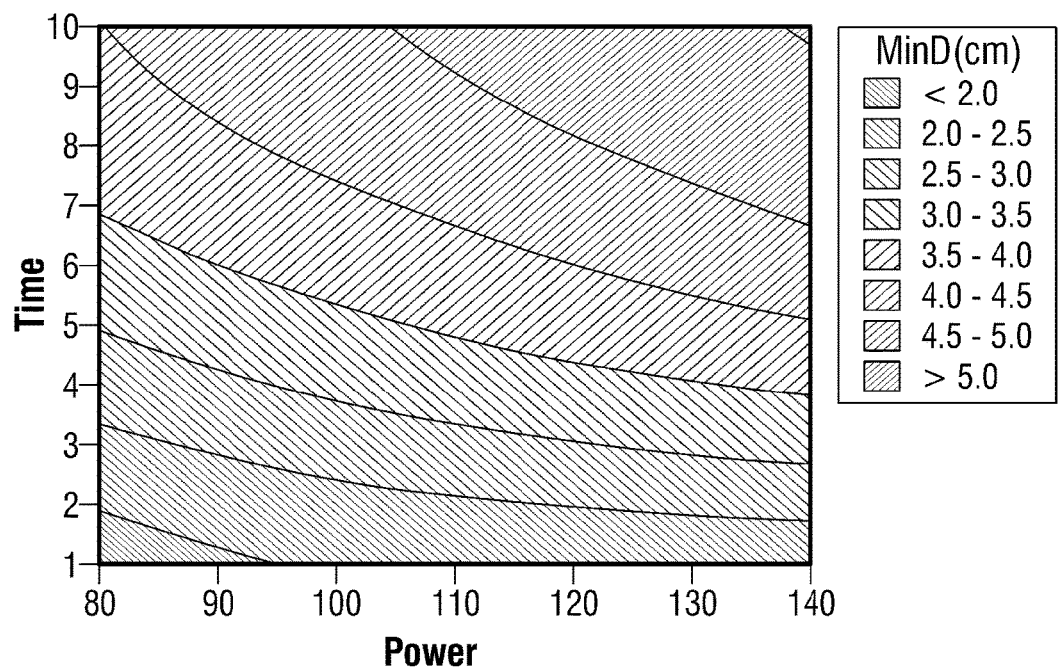
FIG. 5A is a graph in accordance with the present disclosure illustrating a relationship between an ablation diameter, time, and power with respect to a 12 gauge, 915 mHz choked wet tip dipole ablation probe.
Figure 5B:
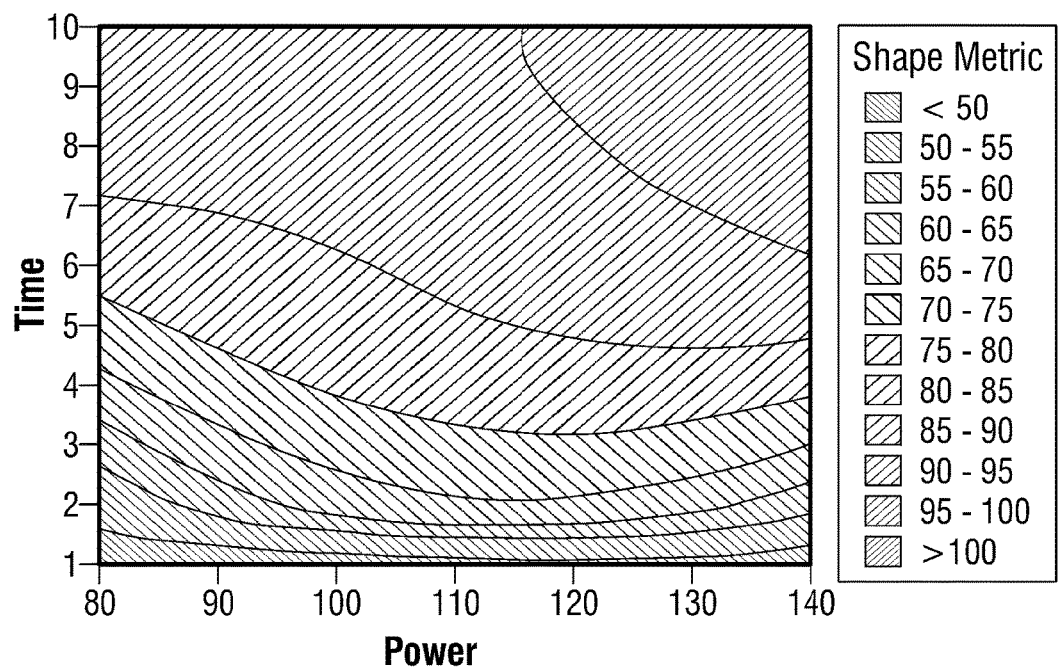
FIG. 5B is a graph in accordance with the present disclosure illustrating a relationship between an ablation shape, time, and power with respect to a 12 gauge, 915 mHz choked wet tip dipole ablation probe.
Figure 6A:
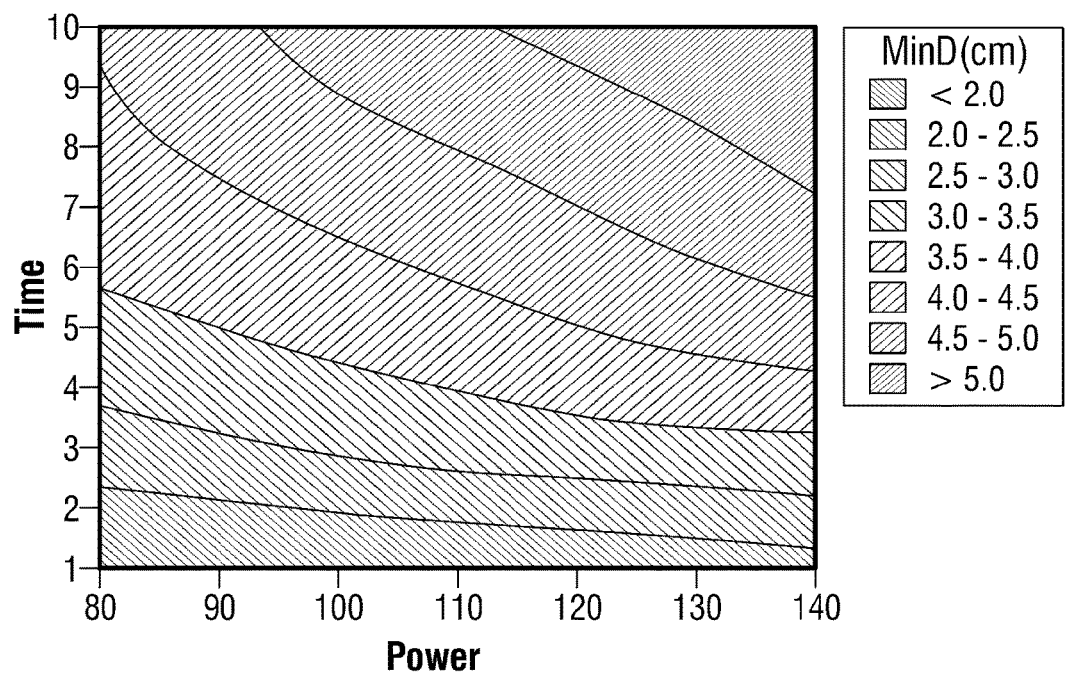
FIG. 6A is a graph in accordance with the present disclosure illustrating a relationship between an ablation diameter, time, and power with respect to a 12 gauge, 2450 mHz choked wet tip dipole ablation probe.
Figure 6B:
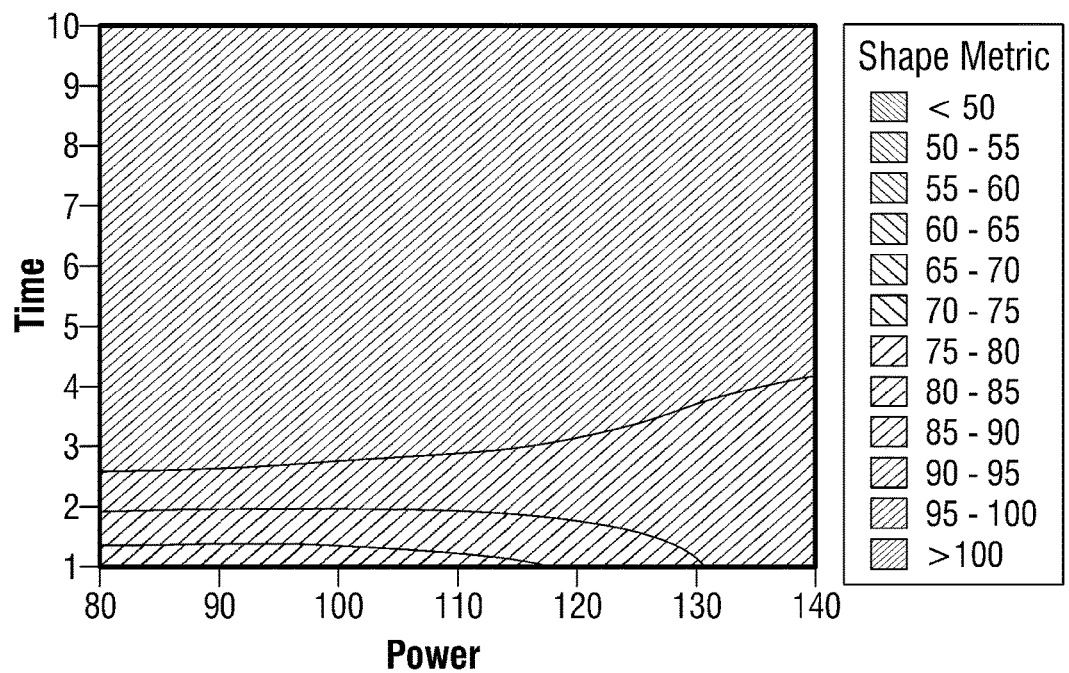
FIG. 6B is a graph in accordance with the present disclosure illustrating a relationship between an ablation shape, time, and power with respect to a 12 gauge, 2450 mHz choked wet tip dipole ablation probe.
Figure 7A:
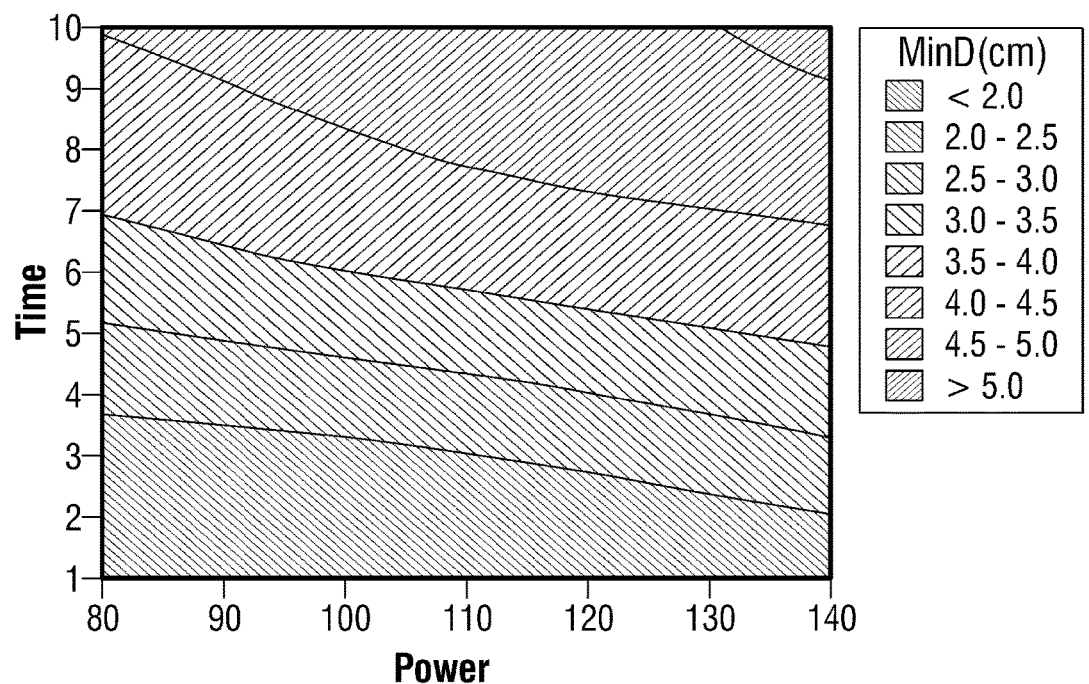
FIG. 7A is a graph in accordance with the present disclosure illustrating a relationship between an ablation diameter, time, and power with respect to a 14 gauge, 915 mHz choked wet tip dipole ablation probe.
Figure 7B:
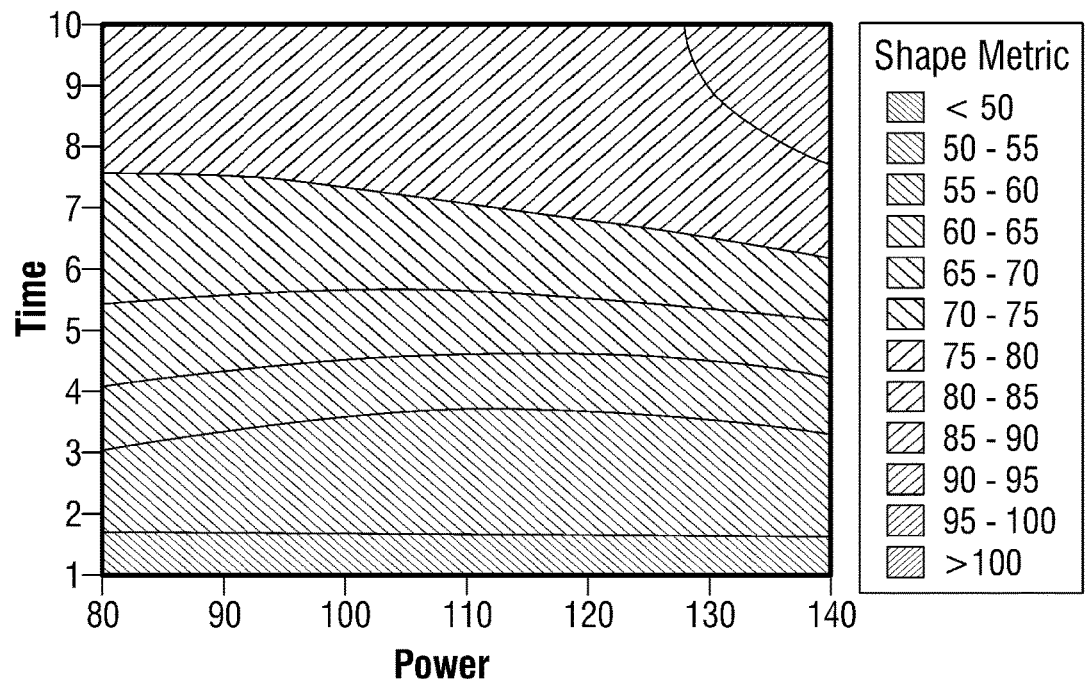
FIG. 7B is a graph in accordance with the present disclosure illustrating a relationship between an ablation shape, time, and power with respect to a 14 gauge, 915 mHz choked wet tip dipole ablation probe.
Figure 8A:
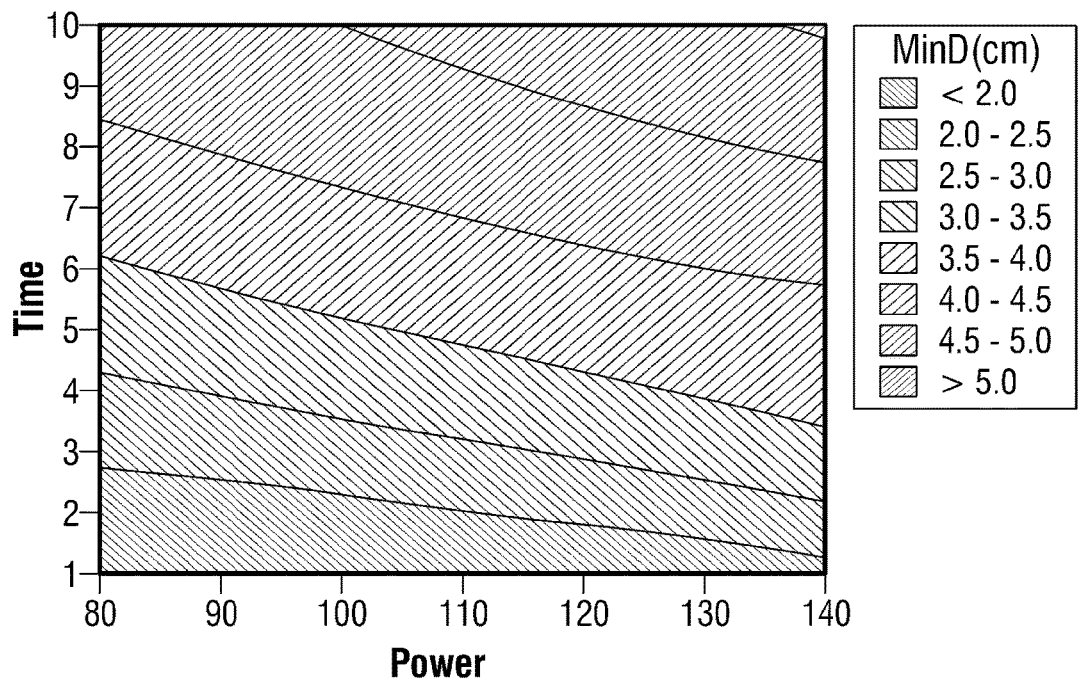
FIG. 8A is a graph in accordance with the present disclosure illustrating a relationship between an ablation diameter, time, and power with respect to a 14 gauge, 2450 mHz choked wet tip dipole ablation probe.
Figure 8B:
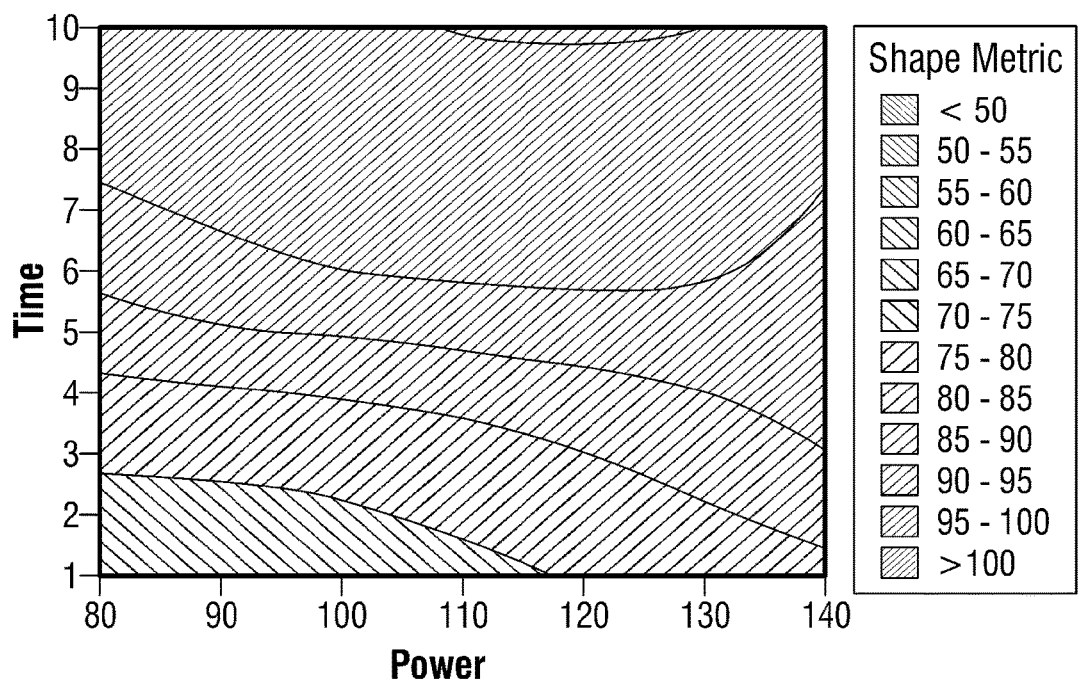
FIG. 8B is a graph in accordance with the present disclosure illustrating a relationship between an ablation shape, time, and power with respect to a 14 gauge, 2450 mHz choked wet tip dipole ablation probe.

Turning now to FIGS. 5A, 5B, 6A, 6C, 7A, 7D, 8A, and 8B, examples of measures minimum ablation diameter and shape metric are shown with respect to probe diameter and operating frequency. FIG. 5A illustrates a relationship between an ablation diameter, time, and power of a 12 gauge diameter, 915 mHz choked wet tip dipole ablation probe. FIG. 5B is a graph illustrating a relationship between an ablation shape, time, and power of a 12 gauge, 915 mHz choked wet tip dipole ablation probe. FIG. 6A illustrates a relationship between an ablation diameter, time, and power of a 12 gauge diameter, 2450 mHz choked wet tip dipole ablation probe. FIG. 6B is a graph illustrating a relationship between an ablation shape, time, and power of a 12 gauge, 2450 mHz choked wet tip dipole ablation probe. FIG. 7A illustrates a relationship between an ablation diameter, time, and power with respect to a 14 gauge, 915 mHz choked wet tip dipole ablation probe. FIG. 7B is a graph illustrating a relationship between an ablation shape, time, and power with respect to a 14 gauge, 915 mHz choked wet tip dipole ablation probe. FIG. 8A depicts a relationship between an ablation diameter, time, and power with respect to a 14 gauge, 2450 mHz choked wet tip dipole ablation probe. FIG. 8B shows a relationship between an ablation shape, time, and power with respect to a 14 gauge, 2450 mHz choked wet tip dipole ablation probe.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for planning an ablation procedure, the system comprising:
    a plurality of ablation probes; and
    a generator configured to couple to at least one of the plurality of ablation probes, the generator including:
        a generator module configured to generate energy suitable for ablating tissue;
        a display configured to display a user interface, the user interface configured to receive a user-selectable ablation shape and at least one probe parameter; and
        a processor configured to select at least one of the plurality of ablation probes suitable for forming an ablation volume corresponding to the user-selectable ablation shape based on the at least one probe parameter, the processor being further configured to signal the display to preview the at least one selected ablation probe.

2. The system according to claim 1, further comprising:
    a storage device coupled to the processor and configured to store a database of a plurality of probe parameters.

3. The system according to claim 1, wherein the at least one probe parameter is selected from the group consisting of a probe diameter, a frequency, an ablation dimension, and a temporal coefficient.

4. The system according to claim 2, further comprising:
    a data interface coupled to the storage device, the data interface configured to couple to an external device storing an updated plurality of probe parameters.

5. The system according to claim 4, wherein the data interface is further configured to automatically synchronize the database with the updated plurality of probe parameters.

6. The system according to claim 1, wherein the user interface includes a rotation user interface element configured to rotate the user-selectable ablation shape.

7. The system according to claim 1, wherein the user interface includes a temporal user interface element configured to display an animated depiction of the user-selectable ablation shape.

8. The system according to claim 7, wherein the temporal user interface element includes a user-adjustable slider corresponding to a time scale of the animated depiction.

9. A method for planning an ablation procedure, the method comprising:
    displaying a user interface configured to receive a user-selectable ablation shape and at least one probe parameter;
    selecting at least one of a plurality of ablation probes suitable for forming an ablation volume corresponding to the user-selectable ablation shape based on the at least one probe parameter; and
    signaling a display to preview the at least one selected ablation probe.

10. The method according to claim 9, further comprising:
    storing a database of a plurality of probe parameters in a storage device.

11. The method according to claim 9, wherein the at least on probe parameter is selected from the group consisting of a probe diameter, a frequency, an ablation dimension, and a temporal coefficient.

12. The method according to claim 10, further comprising:
    coupling an external device storing an updated plurality of probe parameters to a data interface coupled to the storage device.

13. The method according to claim 12, wherein coupling the external device further includes automatically synchronizing the database with the updated plurality of probe parameters.

14. The method according to claim 9, wherein displaying the user interface further includes displaying a rotation user interface element configured to rotate the user-selectable ablation shape.

15. The method according to claim 9, wherein displaying the user interface further includes displaying a temporal user interface element configured to display an animated depiction of the user-selectable ablation shape.

16. The method according to claim 15, wherein displaying the temporal user interface further includes displaying a user-adjustable slider corresponding to a time scale of the animated depiction.

* * * * *